United States Patent
Abdou

(10) Patent No.: US 7,578,834 B2
(45) Date of Patent: Aug. 25, 2009

(54) DEVICES AND METHODS FOR THE PRESERVATION OF SPINAL PROSTHESIS FUNCTION

(76) Inventor: M. S. Abdou, 7790 Doug Hill, San Diego, CA (US) 92127

( * ) Notice: Subject to any disclaimer, the term of this patent is extended or adjusted under 35 U.S.C. 154(b) by 558 days.

(21) Appl. No.: 11/121,383

(22) Filed: May 3, 2005

(65) Prior Publication Data

US 2005/0273120 A1 Dec. 8, 2005

Related U.S. Application Data

(60) Provisional application No. 60/567,495, filed on May 3, 2004.

(51) Int. Cl.
A61B 17/88 (2006.01)
(52) U.S. Cl. .................. 606/279; 623/17.11; 623/17.16; 606/76
(58) Field of Classification Search ... 623/17.11–17.16; 606/279, 76
See application file for complete search history.

(56) References Cited

U.S. PATENT DOCUMENTS

| | | | |
|---|---|---|---|
| 4,289,123 A | 9/1981 | Dunn | |
| 5,133,717 A | 7/1992 | Chopin | |
| 5,545,164 A | 8/1996 | Howland | |
| 5,616,142 A | 4/1997 | Yuan et al. | |
| 5,681,312 A | 10/1997 | Yuan et al. | |
| 5,749,968 A * | 5/1998 | Melanson et al. | 118/300 |
| 5,795,584 A | 8/1998 | Totakura et al. | |
| 5,928,233 A | 7/1999 | Apfelbaum et al. | |
| 5,993,449 A | 11/1999 | Schlapfer et al. | |
| 6,010,692 A | 1/2000 | Goldberg et al. | |
| 6,159,244 A | 12/2000 | Suddaby | |
| 6,235,726 B1 | 5/2001 | Burns et al. | |
| 6,294,202 B1 | 9/2001 | Burns et al. | |
| 6,306,136 B1 | 10/2001 | Beccelli | |
| 6,428,576 B1 * | 8/2002 | Haldimann | 623/17.16 |
| 6,508,839 B1 * | 1/2003 | Lambrecht et al. | 623/17.16 |
| 6,521,223 B1 | 2/2003 | Calias et al. | |
| 6,524,315 B1 | 2/2003 | Selvitelli et al. | |
| 6,531,146 B2 | 3/2003 | Calhoun et al. | |
| 6,547,790 B2 | 4/2003 | Harckey, III et al. | |
| 6,599,295 B1 | 7/2003 | Tornier et al. | |
| 6,673,362 B2 | 1/2004 | Calhoun et al. | |

(Continued)

FOREIGN PATENT DOCUMENTS

WO 2004/032726 4/2004

(Continued)

Primary Examiner—Eduardo C Robert
Assistant Examiner—Julianna N. Harvey
(74) Attorney, Agent, or Firm—Fred C. Hernandez; Mintz, Levin, Cohn, Ferris, Glovsky and Popeo P.C.

(57) ABSTRACT

A barrier is placed across a portion of or across the totality of a spinal implant. The barrier can serve a variety of purposes, including, for example: (1) to keep tissue away from the implant and minimize or eliminate the likelihood of tissue adhesion with the spine or implant; (2) to decrease or eliminate the likelihood of tissue growth, migration, invasion and/or interaction with the implant; (3) to decrease or eliminate the likelihood of the dissemination of implant wear debris and particles away from the implant and into body cavities; and (4) to decrease or eliminate the likelihood of calcification, ossification, and/or bone formation adjacent to the implant.

4 Claims, 3 Drawing Sheets

U.S. PATENT DOCUMENTS

| | | |
|---|---|---|
| 2002/0055741 A1 | 5/2002 | Schlapfer et al. |
| 2002/0099386 A1 | 7/2002 | Beger et al. |
| 2002/0183755 A1 | 12/2002 | Michelson et al. |
| 2003/0018389 A1 | 1/2003 | Castro et al. |
| 2003/0078583 A1 | 4/2003 | Biedermann et al. |
| 2004/0133207 A1 | 7/2004 | Abdou |
| 2004/0204713 A1 | 10/2004 | Abdou |
| 2005/0004573 A1 | 1/2005 | Abdou |
| 2005/0021029 A1* | 1/2005 | Trieu et al. .................... 606/61 |
| 2005/0021040 A1 | 1/2005 | Bertagnoli |
| 2005/0119747 A1 | 6/2005 | Fabris Monterumici et al. |
| 2005/0177163 A1 | 8/2005 | Abdou |
| 2005/0288669 A1 | 12/2005 | Abdou |
| 2006/0074488 A1 | 4/2006 | Abdou |
| 2006/0149278 A1 | 7/2006 | Abdou |
| 2006/0217710 A1 | 9/2006 | Abdou |
| 2006/0229615 A1 | 10/2006 | Abdou |
| 2007/0093828 A1 | 4/2007 | Abdou |
| 2007/0106383 A1 | 5/2007 | Abdou |
| 2007/0123884 A1 | 5/2007 | Abdou |

FOREIGN PATENT DOCUMENTS

| | | |
|---|---|---|
| WO | 2004/062482 | 7/2004 |
| WO | 2004/093702 | 11/2004 |
| WO | WO 2005/122922 | 12/2005 |
| WO | WO 2006/041963 | 4/2006 |
| WO | WO 2006/058221 | 6/2006 |
| WO | WO 2006/089292 | 8/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |

\* cited by examiner

DEVICES AND METHODS FOR THE PRESERVATION OF SPINAL PROSTHESIS FUNCTION

REFERENCE TO PRIORITY DOCUMENT

This application claims priority of U.S. Provisional Patent Application Ser. No. 60/567,495 entitled "A Method for the Prevention of Tissue Growth Adjacent to Spinal Implants", filed May 3, 2004. Priority of the filing date of May 3, 2004 is hereby claimed, and the disclosure of the Provisional Patent Application is hereby incorporated by reference.

BACKGROUND

The present disclosure is directed at spinal implants and methods for the preservation of implant function.

Whether for degenerative disease, traumatic disruption, infection or neoplastic invasion, surgical reconstructions of the bony skeleton are common procedures in current medical practice. Regardless of the specifics of the individual operation, many surgeons employ bone grafts and an implantable device to bridge the diseased segment and provide structural support for the remaining skeleton. While the device provides immediate support, long term stability is critically dependant on the formation of a bony bridge across the defect. Using this strategy, diseased segments within the spinal column are similarly repaired using bone grafts and implantable devises. These implants are especially useful in spinal surgery where they can restore spinal alignment and provide immediate stability for the spinal column.

The end result of these operative procedures is bony fusion. That is, a segment of continuous bone is formed between the spinal segment above and below the diseased region. Bony fusion reconstitutes the load bearing capability of the spinal column but destroys the segmental mobility that is characteristic of normal spinal function. Consequently, segmental fusion alters the balance of forces across the spine and necessarily increases the forces acting upon the motion segments above and below the fused region. These load alterations are significant and will accelerate the formation of degenerative changes within the adjacent segments. With time, these segments will also require fusion.

The increase in the rate of degeneration at the spinal segments adjacent to a fused segment has been termed "adjacent segment disease" and presents a significant clinical problem. Approximately 30% of patients who undergo spinal fusion will require fusion of an adjacent segment within 10 years of the original operation. In turn, the extended fusion will redistribute force across neighboring segments and lead to their degeneration, thereby setting up a vicious cycle whereby bony fusion begets additional fusion.

To address this growing problem, there has been interest in devices that can span the diseased spinal region and recreate the motion characteristics of the normal spine. These efforts at motion preservation have lead to the recent introduction of artificial disc devices capable of mimicking the normal movements of the intra-vertebral disc. Surgical implantations of these artificial discs have yielded promising results in both US and European trials. However, the growing experience with these implants has also uncovered factors that complicate the surgical procedure and can lead to premature device failure.

Since the mobile implants are larger and must be placed more precisely than fusion devices, the surgical implantation procedure is necessarily more demanding. An optimal access route to the spine must be used because an indirect approach will only add to the technical difficulty. Since the spinal cord and/or spinal nerves lie behind the vertebral bodies, an anterior approach to the spine provides the most direct and unfettered access to the vertebral disc space. Understandably, all "artificial" discs in current use require placement through an anterior approach.

There is extensive experience with anterior spinal surgery from the current placement of fusion devices and a general recognition of the potential risks inherent in this approach. Since the spinal column is situated posteriorly within the body, an anterior approach requires dissection through the many other structures that lie anterior to the spine. This has proven most challenging in the chest and abdomen where the body's largest blood vessels, the aorta and vena cava, lie immediately anterior and lateral to the spine. Nevertheless, growing surgical experience has reduced the risk to these vessels and other thoraco-abdominal structures to acceptable levels with initial operation. However, scar formation greatly increase the risk of re-operation. With estimates of major vascular injury rates at 30%, the risk of mortality or significant morbidity at second operation is high. For this reason, surgeons currently address a failed anterior fusion by applying a posterior approach at re-operation and thereby avoid the prohibitive risks of recurrent anterior surgery.

The difficulties with re-operative anterior spinal fusion surgery are magnified when motion preservation devices are used. Since these devices are larger than fusion implants, a larger dissection field is needed to place them and the increased dissection leads to a wider region of scar formation. In fusion surgery, the implanted device immobilizes the spine and bears load until the bone graft has healed. Once fused, the newly formed bone effectively shields the implant and, consequently, time-dependant implant fatigue does not occur. However, devices that recreate spinal mobility are designed to replicate complex movement in various planes and are generally implanted in younger patients than the fusion group. They must withstand millions of cycles of repetitive loading as well as endure significant moment arms and shear forces. While fusion devices are expected to withstand those forces until bone fusion occurs, motion preservation devices will be subjected to these forces for the duration of their functional life. Consequently, some implants will dislodge, wear and fail. Since implant replacement through a posterior approach is not possible, patients with failed implants will be subjected to the significant risks of re-operative anterior surgery.

Motion preservation devices contain moving parts and scar in-growth into the device will interfere with proper movement and greatly increase the likelihood of implant failure. In addition, calcification within the scar tissue or within the disc space adjacent to the implant will create a fusion mass around the device and render it useless. Consequently, control of local scar formation, calcification and tissue growth into the implant is imperative. Failure to do so will greatly increase the likelihood of implant failure and require that patients be subjected to additional surgery with substantial risks.

Lastly, all moving components will inevitably produce wear debris and spinal motion preservation devices will also shed particulates. Experience from knee and hip prosthesis has shown that wear particles can lead to bone breakdown and implant loosening, can produce local tissue inflammation and toxicity, and can disseminate through the blood stream to distant organs. Consequently, limitation and containment of the wear debris is important in biological implants. It is even more important in devices placed adjacent to the nervous system, such as spinal implants.

U.S. Pat. Nos. 6,673,362; 6,531,146; 6,521,223; 6,294,202; 6,235,726; 6,010,692 and 5,795,584 all disclose methods for the attenuation of scar formation during post-operative healing. These and other prior art patents describe various compounds, agents and methods that decrease adhesions between two or more tissues. None of these patents teach the use of the agents and methods to prevent adhesions between a tissue and a movable implant, to minimize tissue invasion into the implant, to inhibit bone formation within tissue adjacent to the implant, or to contain wear debris shed by the implant.

SUMMARY

A method for the use of biological barriers around the implant is described. Use of this technique will protect the implant from local tissue invasion and reduce the risk of bone formation around it. Both of these factors will reduce the likelihood of implant failure and the possibility of revision surgery. However, if re-operation is required, this method will also reduce the extent of scar formation around the implant and minimize the potentially lethal risks of additional surgery.

Adoption of the method disclosed in this application will increase the functional life expectancy of the motion preservation implants, minimize the toxic effects of wear debris, and significantly decrease the risks of surgical replacement.

In one aspect, there is disclosed a method of preserving functionality of a spinal implant, comprising identifying a dissection field adjacent to the spinal implant; and positioning a barrier in at least a portion of the dissection field so as to substantially decrease the likelihood of tissue interaction with the spinal implant.

In another aspect, there is disclosed a method of preserving functionality of a spinal implant, comprising identifying a spinal implant; and interposing a barrier between the spinal implant and tissue adjacent the implant to prevent the spinal implant from interacting with the tissue.

In another aspect, there is disclosed a method of preserving functionality of a spinal implant of a subject, comprising placing a barrier in at least a portion of a dissection field adjacent to the spinal implant to decrease the likelihood the implant adversely interacting with a portion of the subject's body.

The details of one or more embodiments are set forth in the accompanying drawings and the description below. Other features, objects, and advantage will be apparent from the description and drawings, and from the claims.

DESCRIPTION OF DRAWINGS

Like reference symbols in the various drawings indicate like elements.

DETAILED DESCRIPTION

The present disclosure is directed at methods and devices for controlling tissue growth and scar formation adjacent to and into spinal implants. While the disclosed methods and devices may be applied at any spinal segment, they are especially applicable in the lumbar spine, where the problems enumerated above are most acute and where no effective clinical strategy currently exists to combat these problems. Furthermore, the disclosed methods and devices are suitable for use in both human and animal subjects.

Pursuant to an exemplary implementation, an anterio-lateral exposure of a patient's spine is performed to expose a disc space for implantation of an implant (such as, for example, an artificial disc) into the space. As discussed, once implanted, the artificial disc implant mimics the normal movement of an intra-vertebral disc. The implant is placed in the disc space pursuant to any of a variety of processes known to those skilled in the art. In a next step, a barrier is placed across a portion of or across the totality of the implant, as described in detail below. The barrier can serve a variety of purposed, including, for example: (1) to keep tissue away from the implant and minimize or eliminate the likelihood of tissue adhesion with the spine or implant; (2) to decrease or eliminate the likelihood of tissue growth, migration, invasion and/or interaction with the implant; (3) to decrease or eliminate the likelihood of the dissemination of implant wear debris and particles away from the implant and into body cavities; and (4) to decrease or eliminate the likelihood of calcification, ossification, and/or bone formation adjacent to the implant. These are described in more detail below.

Figure 1:
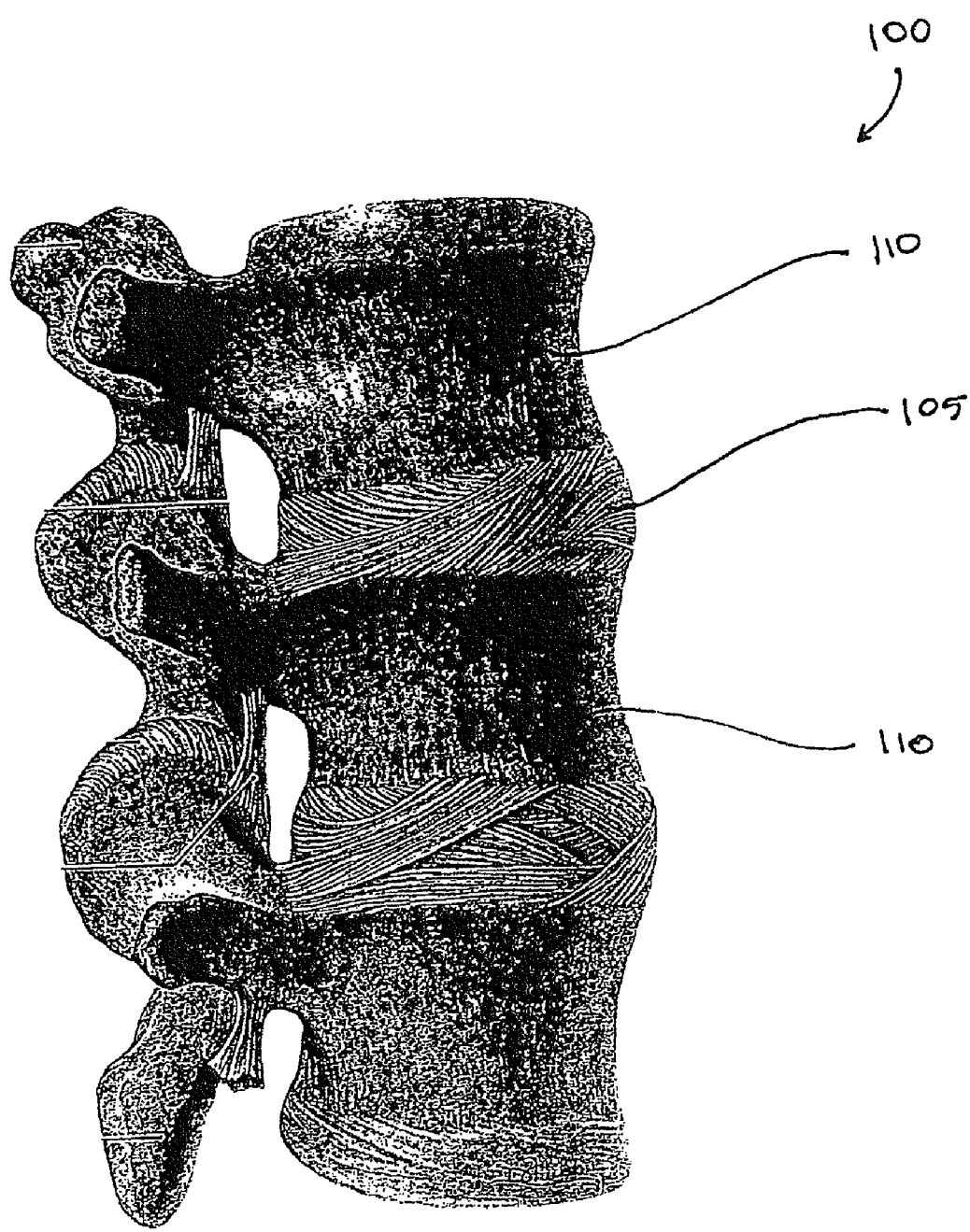
FIG. 1 shows a lateral view of the spine.

FIG. 1 shows a lateral view of a portion of a portion of a spine 100 including an intravertebral disc 105 disposed between two vertebrae 110. Pursuant to a surgical procedure, the disc 105 can be surgically removed to create a space at the location where the disc 105 was previously positioned. Various procedures for removing the disc 105 are known to those skilled in the art and, therefore, are not described in detail herein.

Figure 2:
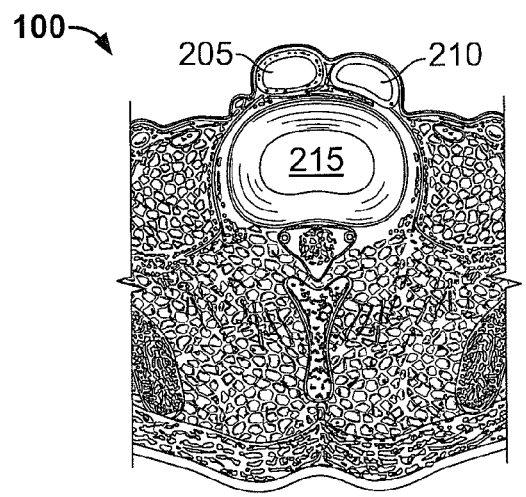
FIG. 2 shows a cross sectional view of the lumbar spine with blood vessels in a normal anatomical position.

During the surgical procedure, the spine 100 is exposed in a well-known fashion to approach and provide anterior access to the spine 100. The approach may be performed through the peritoneum (referred to as trans-peritoneal) or behind the peritoneum (referred to as retro-peritoneal). FIG. 2 shows a cross-sectional view of the lumbar spine 100. It may be necessary to retract one or more anatomical structures to provide unobstructed access to the spine 100. For example, a pair of major blood vessels, the vena cava 205 and the aorta 210, are disposed immediately anterior and lateral to the spine 100. The vena cava 205 and the aorta 210 must be retracted in order to provide access to the intravertebral disc and the disc space 215 where the implant device will be positioned. Alternately, the spine can be approached laterally.

Figure 3:
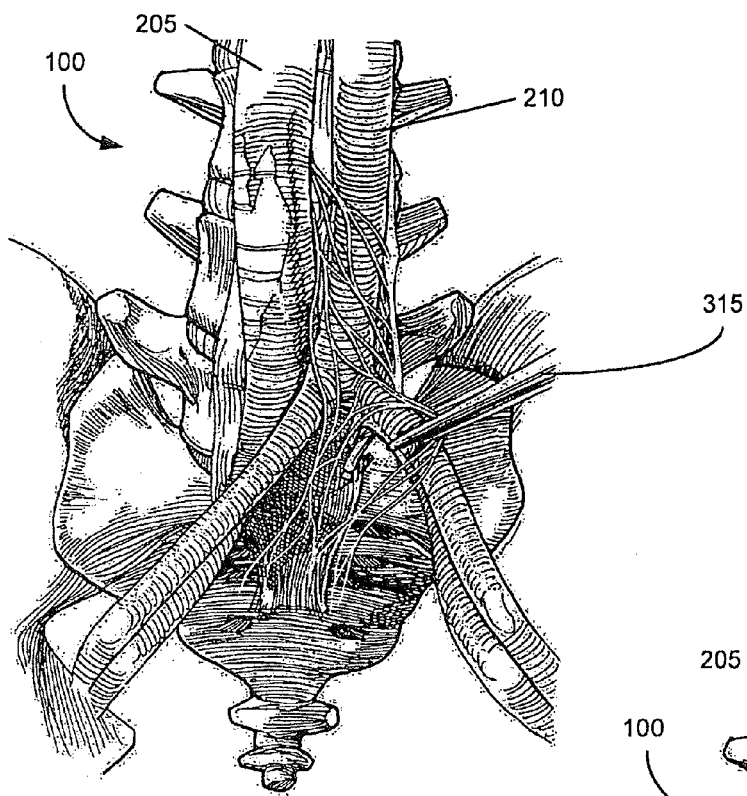
FIG. 3 is a view of the anterior aspect of the lower lumbar spine with an instrument illustrating spinal access between blood vessels.
Figure 4:
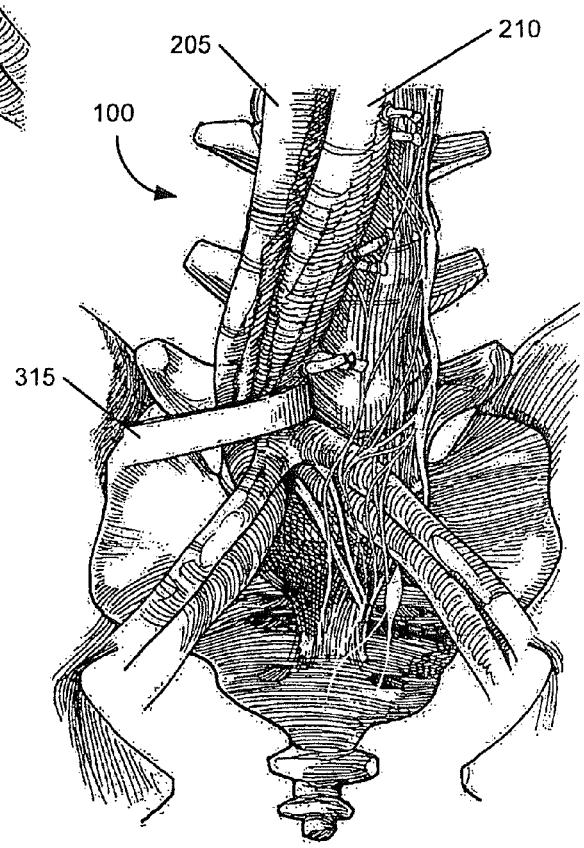
FIG. 4 is a view of the anterior aspect of the lower lumbar spine with an instrument illustrating spinal access lateral to the vessels.

The retraction of the vessels is described in more detail with reference to FIGS. 3 and 4, which show the anterior aspect of the lower lumbar spine 100 with blood vessels (the vena cava 205 and the aorta 210) positioned immediately anterior and lateral to the spine 100. In a first implementation, shown in FIG. 3, at least one retractor instrument 315 engages one or more of the blood vessels to move the blood vessels and provide access to the spine 100. The retractor instrument 315 is used to expose a disc space in the spine 100 by widening a v-shaped space formed between the vessels. In another implementation, shown in FIG. 4, the retractor instrument 315 engages both vessels. The retractor instrument 315 exposes the disc space by retracting the vena cava 205 and the aorta 210 together to one side of the spine 100. It should be appreciated that other types of procedures and mechanisms can be used to expose the disc space in the spine and that this disclosure is not limited to use of a retractor instrument as described herein.

Figure 5:
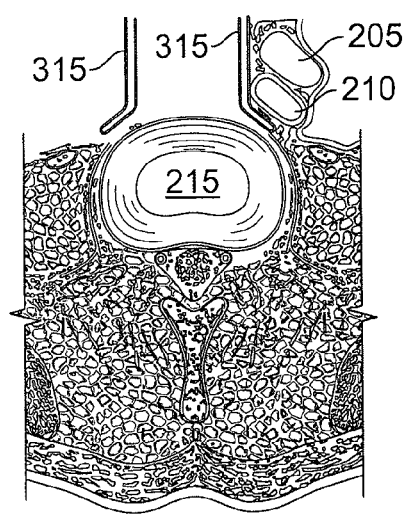
FIG. 5 demonstrates retractor placement lateral to vessels and exposure of a disc space.
Figure 6:
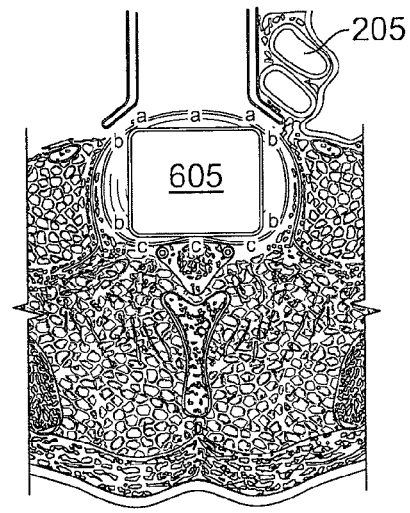
FIG. 6 demonstrates exposure of the disc space and placement of a spinal implant, as well as potential placement locations of one or more barriers to tissue growth.

FIG. 5 shows a cross-sectional view of the spine 100 with the retractor instrument 315 retracting the vena cava 205 and the aorta 210 to expose the disc space 215. After the disc space 215 is exposed, a discectomy is performed and an implant device 605 (such as an artificial disc) is placed in the disc space 215 pursuant to any procedure known to those skilled in the art. FIG. 6 shows a cross-sectional view of the lumbar spine 100 with the implant device 605 positioned in the disc space. A dissection field is located adjacent to the implant device 605. The dissection field includes an anterior region (identified by the reference numerals "a" in FIG. 6), a pair of side or lateral regions (identified by the reference numerals "b" in FIG. 6), and a posterior region (identified by the reference numerals "c" in FIG. 6). The dissection field surrounds at least a portion of the implant device 605

Pursuant to one aspect of the disclosed method, a biological barrier is positioned across a portion of or across the totality of the dissection field. The barrier is placed prior to return of the blood vessels 205, 210 to their native anatomical position. As described below, the biological barrier provides an obstacle or shield between at least a portion of the implant device 605 and the anatomy adjacent or near the implant device 605.

Figure 7:
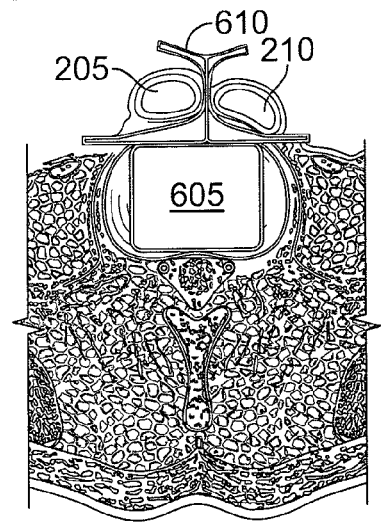
FIG. 7 shows an anterior barrier in place after disc space access through the space between the vessels.

The barrier can be positioned in various manners relative to the implant device 605. For example, the barrier can be placed so that it is disposed across the side of the vessels and partially raps around the vessels. In an implementation shown in FIG. 7, the barrier 610 is positioned at least partially between the vessels 205, 210, such as after a midline (between the vessels) approach to the disc space. In another implementation, shown in FIG. 8, the barrier 610 is positioned lateral to the vessels 205, 210, such as after a lateral-to-vessel approach to the disc space.

Figure 8:
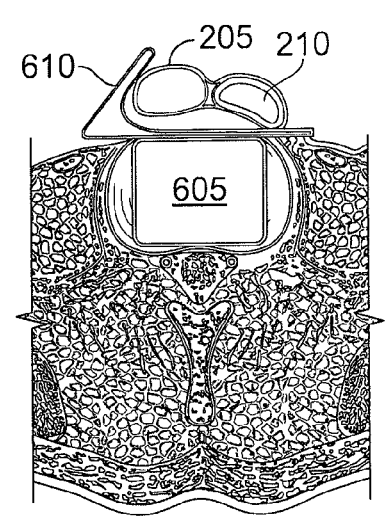
FIG. 8 shows the anterior barrier in place after disc space access lateral to the vessels.

Although FIG. 8 shows the approach to on one side of the blood vessels 205 and 210, it is understood that the method can be similarly applied when the approach is from the other side of the vessels. This permits re-dissection along a barrier plane 705 separating the vessels 205, 210 and the implant device 605 at a later date. Placement along the initial dissection planes will advantageously help preserve those planes for re-dissection. Moreover, if a solid non-absorbable barrier material is used (as described below), it can be used to hold the vessels when accessing the disc space at re-operation, if necessary. In addition, the barrier will serve to limit tissue growth into the device and prevent the device's wear debris from spilling into the abdominal cavity, as described more fully below.

It should be appreciated that the barrier can be positioned at any of a variety of location along the dissection field. For example, the barrier can be placed along the sides regions "b" or along the posterior region "c" (shown in FIG. 6) of the dissection field. Placement of the barrier in along the side or posterior region limits tissue growth into the implant device 605, reduces the likelihood of calcification and fusion formation, and thereby preserves implant function, as described more fully below.

Use of the barrier around the implant device provides a variety of advantages over schemes where an implant device is used without a barrier. For example, the barrier keeps adjacent tissue away from contact with the implant device and the spine. This decreases the likelihood of tissue adhesion with the spine and/or the implant device thereby decreasing the likelihood of implant failure and the need for re-dissection. The barrier also decreases tissue growth or migration into the implant. That is, the barrier prevents adjacent tissue from interacting with or interfering with the implant functionality. This can be important, as such interference can degrade the implant or cause the implant to fail.

As mentioned, the implant devices are often designed to replicate complex movement in various planes and must withstand millions of cycles of repetitive loading, as well as endure significant moment arms and shear forces. Consequently, the repetitive movement can produce wear debris and cause the implant to shed particulates. In devices placed adjacent to the nervous system, such as spinal implants, the debris can cause significant injury, such as if the debris migrates into body cavities such as the abdominal cavity. Advantageously, use of the barrier around the implant blocks such debris from migrating away from the implant.

In addition, use of the barrier around the implant decreases the likelihood of ossification and bone formation adjacent the implant. Such ossification or bone formation can form a mass around the implant device, which can render the implant device useless. The barrier advantageously decreases or entirely eliminates the likelihood of such a mass forming. Thus, use of the barrier around spinal implant significantly increases the functional life expectancy of the device, minimizes the toxic effects of its wear debris, and significantly decrease the risks of surgical device replacement. The aforementioned advantages can be realized whether the implant is placed using the illustrated anterior approach to the spine or any other surgical corridor (i.e., lateral approach, posterior approach, etc.)

The barrier can comprise any structure or composition that provides shields, blocks, or otherwise prevents tissue migration or adhesion between adjacent tissue and the implant device. The barrier can also comprise any structure or composition that prevents migration of debris from the implant device to other parts of the body. Thus, the barrier and any of its components can be made of any biologically adaptable or compatible materials shown to prevent tissue migration, replication and/or adhesion. The barrier may be absorbable or non-absorbable and consist of liquids, gels or solids.

In an exemplary implementation, the barrier comprises one or more of the following substances, including, but not limited to, silastic, ADCON, PTFE, Polymers such as PEO and PBT, copolymers having recurrent carbon units, polymers/composites of hyaluronic acid, cross-linked polyanionic gels, copolymers derived from trimethylene carbonate, non-woven fabric in adherent contact with a foam, mesh, web or woven fabric, polymers of polylactide polymers and the like. The barrier or its components may be partially or entirely coated or made with pharmaceuticals and/or immuno-modulators (steroids, etc.), growth factors (PDGF, EGF, TGF, BMP, FGF, combination agents and the like), sense and anti-sense genetics, cells and/or cellular products that could enhance its inhibition of tissue growth, migration, invasion and particulate containment. It should be appreciated that other future-developed agents, compounds, biologics, devices and the like can serve as barriers to tissue growth. The method illustrated is equally applicable to those developed.

In summary, use of a biological barrier around a motion preservation spinal implant will significantly increase the functional life expectancy of the device, minimize the toxic effects of its wear debris, and significantly decrease the risks of surgical device replacement. As these devices move into wider clinical application, it is imperative that methods be devised to maximize proper implant function and minimize the risks of replacement surgery.

A number of embodiments of the invention have been described. Nevertheless, it will be understood that various modifications may be made without departing from the spirit and scope of the claims. Accordingly, other embodiments are within the scope of the following claims.

What is claimed is:

1. A method to facilitate re-dissection and re-operation through soft tissues that are outside of a spinal column in order to promote positioning or replacement of a spinal prosthesis, wherein at least a segment of the soft tissues are contained within a dissection field created at a first operation to access the spinal column and implant a spinal prosthesis, comprising:

creating a surgical corridor through the soft tissues outside of the spinal column in order to access an exterior aspect of the inter-vertebral disc between a first and a second vertebra;

accessing the exterior aspect of the disc space and creating a defect in the annulus fibrosis;

removing at least a portion of an inter-vertebral disc material from the interior aspect of the disc space;

implanting a spinal prosthesis within the disc space, wherein the spinal prosthesis is adapted to at least provide partial support of the spinal column;

identifying a segment of the dissection field that is outside of the spinal column and the annulus fibrosis; and positioning a barrier within a portion of the identified segment of the dissection field that resides outside of the spinal column, wherein the barrier at least partially inhibits scar formation within the soft tissues outside of the spinal column and facilitates re-operation through the soft tissues.

2. A method as in claim 1, wherein the spinal prosthesis is an artificial disc that maintains motion between the first and second vertebrae.

3. A method as in claim 1, wherein the barrier decreases the dissemination of wear debris for the spinal implant into a body cavity.

4. A method as in claim 1, wherein the barrier decreases the likelihood of calcification, ossification, or bone formation.

* * * * *